United States Patent [19]

Nowack et al.

[11] Patent Number: 4,570,025

[45] Date of Patent: Feb. 11, 1986

[54] PREPARATION OF ALKENES AND CYCLOALKENES

[75] Inventors: Gerhard P. Nowack; Marvin M. Johnson, both of Bartlesville, Okla.

[73] Assignee: Phillips Petroleum Company, Bartlesville, Okla.

[21] Appl. No.: 744,703

[22] Filed: Jun. 14, 1985

[51] Int. Cl.$^4$ .............................. C07C 5/03; C07C 5/05
[52] U.S. Cl. ...................... 585/259; 585/277; 502/208
[58] Field of Search ............... 585/259, 250, 275, 277; 502/208

[56] References Cited

U.S. PATENT DOCUMENTS

| | | | |
|---|---|---|---|
| 3,177,151 | 4/1965 | Calvert | 252/435 |
| 3,254,134 | 5/1966 | Smith et al. | 260/667 |
| 3,308,054 | 3/1967 | Duir et al. | 205/89 |
| 3,360,577 | 12/1967 | Pickles | 260/666 |
| 3,468,953 | 9/1969 | Besson et al. | 260/583 |
| 3,485,887 | 12/1969 | Kronig et al. | 260/677 |
| 3,674,886 | 7/1972 | Komatsu et al. | 585/277 |
| 3,804,916 | 4/1974 | Lalancette | 260/677 H |
| 3,857,894 | 12/1974 | Morelli et al. | 260/666 A |
| 3,904,550 | 9/1975 | Pine | 208/217 |
| 3,994,986 | 11/1976 | Koto et al. | 260/666 A |
| 4,162,271 | 7/1979 | Wideman | 585/274 |
| 4,204,081 | 5/1980 | Menspace | 585/274 |
| 4,347,392 | 8/1982 | Cosyns et al. | 585/259 |
| 4,364,854 | 12/1982 | McDaniel et al. | 252/437 |
| 4,364,855 | 12/1982 | McDaniel et al. | 252/437 |
| 4,517,395 | 5/1985 | Obenaus et al. | 585/259 |

Primary Examiner—John Doll
Assistant Examiner—A. Pal
Attorney, Agent, or Firm—K. K. Brandes

[57] ABSTRACT

In one embodiment, an alkadiene and/or alkatriene is contacted with a free hydrogen containing gas in the presence of a catalyst composition comprising (a) palladium metal and (b) aluminum phosphate, so as to form primarily an alkene. In another embodiment, a cycloalkadiene and/or cycloalkatriene is contacted with a free hydrogen containing gas in the presence of a catalyst composition comprising (a) palladium metal and (b) aluminum phosphate, so as to form primarily a cycloalkene. The preferred cycloalkadiene is 1,5-cyclooctadiene, and the preferred cycloalkene is cyclooctene. Optionally, an alkali metal alkoxide, e.g. lithium methoxide, and/or carbon monoxide can be present during the hydrogenation reactions to improve the selectivity to alkenes and cycloalkenes, respectively.

26 Claims, 2 Drawing Figures

PREPARATION OF ALKENES AND CYCLOALKENES

BACKGROUND OF THE INVENTION

This invention relates to a process for preparing alkenes and cycloalkenes. In one aspect, this invention relates to the selective hydrogenation of alkadienes and of alkatrienes to alkenes. In another aspect, this invention relates to the selective hydrogenation of cycloalkadienes and of cycloalkatrienes to cycloalkenes. In still another aspect, this invention relates to the use of a supported palladium catalyst in the hydrogenation of cyclodiolefins.

Processes for the selective catalytic hydrogenation of alkadienes to alkenes and of cycloalkadienes to cycloalkenes over supported palladium catalysts have been disclosed, e.g., in U.S. Pat. Nos. 3,857,894, 3,804,916 and 3,360,577. However, there is an ever present need to develop new processes utilizing catalysts that aze more active and/or more selective for the production of alkenes and cycloalkenes than catalysts known in the art.

SUMMARY OF THE INVENTION

It is an object of this invention to convert alkadienes and/or alkatrienes to alkenes in high yields. It is another object to convert cycloalkadienes and/or cycloalkatrienes to cycloalkenes in high yields. It is another object of this invention to provide a new process employing a supported palladium catalyst which is more selective for the formation of alkenes and cycloalkenes, respectively, than previously used palladium-containing hydrogenation catalysts. It is a further object of this invention to selectively hydrogenate 1,5-cyclooctadiene to cyclooctene. Other objects and advantages will be apparent from the detailed description and the appended claims.

In accordance with the first embodiment of the present invention, a feed stream comprising at least one hydrocarbon selected from the group consisting of alkadienes (also referred to as diolefins) having from 4 to 12 carbon atoms per molecule and of alkatrienes (also referred to as triolefins) having from 6 to 12 carbon atoms per molecule is contacted with a free hydrogen containing gas, in the presence of a catalyst composition comprising (a) palladium metal and (b) an aluminum phosphate containing support, under such reaction conditions as will result in a reaction product comprising at least one alkene (also referred to as monoolefin) as the major component, wherein the number of carbon atoms per molecule of said alkene, alkadiene and alkatriene is the same.

In accordance with the second embodiment of this invention, a feed stream comprising at least one hydrocarbon selected from the group consisting of cycloalkadienes (also referred to as cyclodiolefins) having from 5 to 12 carbon atoms per molecule and cyclotrienes (also referred to as cyclotriolefins) having from 7 to 12 carbon atoms per molecule is contacted with a free hydrogen containing gas, in the presnece of a catalyst composition comprising (a) palladium metal and (b) an aluminum phosphate containing support, under such reaction conditions as will result in a reaction product comprising at least one cycloalkene (also referred to as cycloolefin) as the major component, wherein the number of carbon atoms per molecule of said cycloalkene, cycloalkadiene and cyclotriene is the same. In a preferred embodiment, a feed stream comprising 1,5-cyclooctadiene is hydrogenated to cyclooctene over the above-described catalyst, in accordance with this invention.

In another embodiment of this invention, carbon monoxide is present during said contacting of an alkadiene and/or alkatriene with a free hydrogen containing gas, in the presence of said catalyst composition. In still another embodiment of this invention, carbon monoxide is present during said contacting of a cycloalkadiene (preferably 1,5-cyclooctadiene) and/or cycloalkatriene with a free hydrogen containing gas, in the presence of said catalyst composition.

In a further embodiment, an alkali metal alkoxide containing from 1 to 4 carbon atoms per molecule (preferably an alkali metal methoxide) is present during said contacting of an alkadiene and/or alkatriene with a free hydrogen containing gas, in the presence of said catalyst composition (and, optionally, carbon monoxide). In a still further embodiment, an alkali metal alkoxide containing from 1 to 4 carbon atoms per molecule (preferably an alkali metal methoxide) is present during said contacting of a cycloalkediene (preferably 1,5-cyclooctadiene) and/or cyclooctatriene with a free hydrogen containing gas, in the presence of said catalyst composition (and, optionally, carbon monoxide). The most preferred alkali metal methoxide is lithium methoxide.

DETAILED DESCRIPTION OF THE INVENTION

Figure 1:
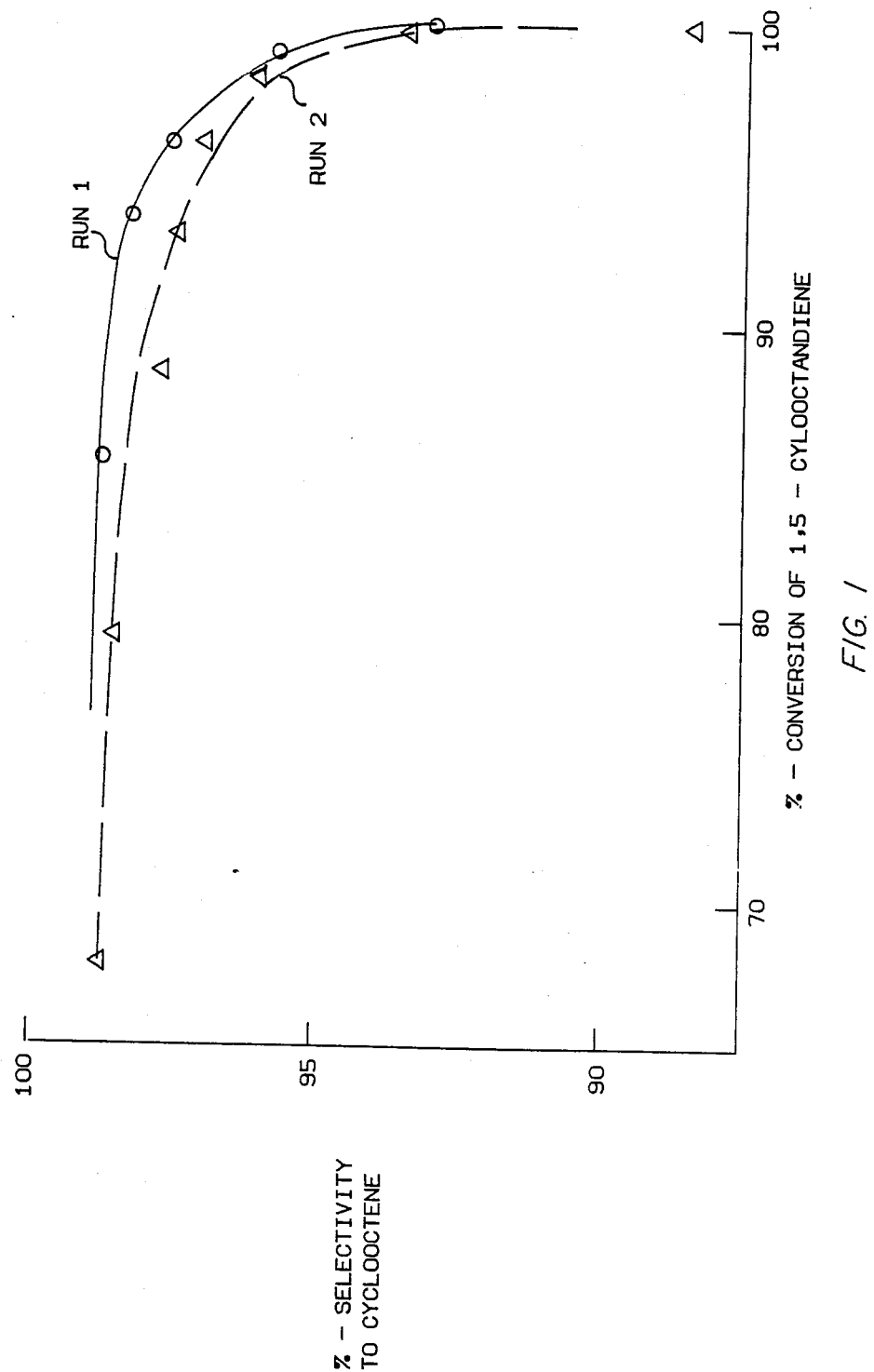
FIG. 1 is a graph showing the correlation of cyclooctadiene conversion and selectivity to cyclooctene.

The catalyst composition employed in the process of this invention, namely the selective hydrogenation of di- and/or triolefins to primarily monoolefins and of cyclodi- and/or cyclotriolefins to primarily cycloolefins, is a composition comprising (a) substantially metallic palladium, and (b) an aluminum phosphate-containing support. Aluminum phosphate can be prepared by any suitable method, generally by precipitation upon mixing of a solution containing $Al^{+3}$ ions (preferably an aqueous solution of $Al(NO_3)_3$) and a second solution containing $H_3PO_4$ or $H_2PO_4^-$ or $HPO_4^{2-}$ or $PO_4^{-3}$ ions (preferably an aqueous solution of $(NH_4)_2HPO_4$) at a suitable pH. Examples of such precipitation methods are those described in U.S. Pat. Nos. 4,364,854 and 4,364,855, and 3,177,151, herein incorporated by reference. The preferred support is aluminum phosphate having a surface area of at least 30 $m^2/g$ (as determined by the $BET/N_2$ method, ASTM D3037) and an Al:P mol ratio ranging from about 0.4:1 to about 1.1:1, more preferably 0.9:1 to 1.1:1.

It is within the scope of this invention to use combinations of aluminum phosphate and other inorganic refractory oxides such as alumina, silica, aluminosilicates, titanium dioxide, and the like. Optionally, the catalyst composition further comprises at least one other hydrogenation component (in addition to palladium) such as metallic platinum, rhenium or nickel.

The catalyst composition employed in this invention can be prepared by any known method of providing substantially metallic palladium on an aluminum phosphate-containing support. Preferably, the aluminum phosphate containing support material is first impregnated with a solution containing a suitable inorganic or organic palladium compound such as palladium(II) nitrate, halide or acetate, plus optionally a salt of at least one other metal such as Pt, Re, Ni. Preferably, a solution of Pd(II) acetate in acetone is used as the impregnating solution. The thus impregnated material is dried and, optionally, calcined in air. The dried, and optionally calcined, material is then heated with a reducing gas, preferably a free hydrogen containing gas, so as to substantially reduce the palladium compound to palladium metal. Typical drying conditions are about 100°–300° F. and about 0.1–10 hours. Typical reducing conditions are about 400°–700° F. and about 0.1–5 hours, using flowing $H_2$. It is within the scope of this invention to employ other methods of depositing palladium on the aluminum phosphate-containing support, e.g., ion exchange and coprecipitation.

The palladium content in the catalyst composition of this invention generally ranges from 0.01 to about 20 weight-%, preferably from about 0.1 to about 10 weight-%, and more preferably from about 0.2 to about 5 weight-%. The surface area (determined by the BET/$N_2$ method, ASTM D3037) of the catalyst composition generally ranges from about 30 to about 200 $m^2/g$, preferably from about 50 to 150 $m^2/g$; and the pore volume (determined by alcohol absorption, as described in Example I) of said catalyst composition generally ranges from about 0.5 to about 3 cc/g, preferably from about 1 to about 2 cc/g.

The feed stream to be hydrogenated in accordance with the first embodiment of this invention can be one comprising of at least one substantially pure diolefin or triolefin. Or it can be a mixture of at least one diolefin and at least one triolefin. An inert substance such as a liquid alkane or cycloalkane can be present in the above-described feed streams. In one preferred embodiment, an alkali metal alkoxide containing 1–4 carbon atoms per molecule (preferably an alkali metal methoxide such as Li methoxide) is present in the diolefin and/or triolefin containing feed as on additional catalytic ingredient to improve the selectivity to monoolefins.

The feed stream to be hydrogenated in accordance with the second embodiment of this invention can be one comprising at least one substantially pure cyclodiolefin or cyclotriolefin. It it can be a mixture of at least one cyclodiolefin and at least one cyclotriolefin. An inert substance such as a liquid alkane or cycloalkane can be present in the above-described feed streams. In one preferred embodiment, an alkali metal alkoxide containing 1–4 carbon atoms per molecule (preferably an alkali metal methoxide, most preferably lithium methoxide) is present in the cyclodiolefin and/or cyclotriolefin containing feed to improve the selectivity to cycloolefins.

It is within the scope of this invention to combine the first and second embodiments and to employ a mixture of at least one diolefin and/or triolefins and at least one cyclodiolefins and/or cyclotriolefin. This mixture is then hydrogenated in accordance with this invention so as to produce a mixture of a least one monolefin and at least one cycloolefin.

The second reactant can be substantially pure hydrogen gas or a mixture of hydrogen and another suitable gas such as an inert gas (e.g., nitrogen). In one preferred embodiment, carbon monoxide is present in the hydrogen containing gas stream, most preferably when one of the above-described feed streams is contacted with the hydrogen containing gas in the presence of a Pd/AlPO$_4$ catalyst composition and lithium methoxide to improve selectivity to either monoolefins or cycloolefins.

The feed hydrocarbon that is employed in the first embodiment of this invention can be any unsubstituted or alkyl-substituted diolefin having from 4–12 carbon atoms or any unsubstituted or alkyl-substituted triolefin having from 6–12 carbon atoms per molecule, such as 1,3-butadiene, 2-methyl-1,3-butadiene, 1,3-pentadiene, 3-methyl-1,3-pentadiene, 1,3-hexadiene, 2,4-hexadiene, 1,3-heptadiene, 2,4-heptadiene, 1,4-heptadiene, 3-methyl-1,4-heptadiene, 1,3-decadiene, 2-methyl-1,3-decadiene, 3-ethyl-1,4-decadiene, 1,3-dodecadiene, 2,4-dodecadiene, 1,4-dodecadiene, 1,3,5-hexatriene, 1,3,5-heptatriene, 1,3,5-octatriene, 2-methyl-1,3,5-octatriene, 1,3,5-decatriene, 1,4,7-decatriene, 2,4-dimethyl-1,3,5-decatriene, 1,3,5-dodecatriene, 2,3,6-dodecatriene, and the like.

The feed hydrocarbon that is employed in the second embodiment of this invention can be any unsubstituted or alkyl-substituted cyclodiolefin having from 5 to 12 carbon atoms per molecule or any cyclotriolefin having from 7 to 12 carbon atoms per molecule such as 1,3-cyclopentadiene, 1,3-cyclohexadiene, 1,4-cyclohexadiene, 1-methyl-1,3-cyclohexadiene, 1-methyl-1,4-cyclohexadiene, 1,3-cycloheptadiene, 1,4-cycloheptadiene, 1,3-cyclooctadiene, 1,4-cyclooctadiene, 1,5-cyclooctadiene, 1-methyl-1,5-cyclooctadiene, 1,3-dimethyl-1,5-cyclooctadiene, 3-ethyl-1,5-cyclooctadiene, 1,5-cyclononadiene, 3-propyl-1,5-cyclononadiene, 1,3-cyclodecadiene, 1,3-cyclododecadiene, 1,3,5-cycloheptatriene, 1-methyl-1,3,5-cycloheptatriene, 1,3,5-cyclooctatriene, 1,3-dimethyl-1,3,5-cyclooctatriene, 1,3,5-cyclodecatriene, 1,4,6-cyclodecatriene, 1-methyl-1,4,6-cyclodecatriene, 1,3,5-cyclododecatriene, 1,5,9-cylododecatriene, and the like.

The presently preferred hydrocarbon feed compounds of this invention are cyclodiolefins. The presently most preferred hydrocarbon feed compound is 1,5-cyclooctadiene.

The hydrocarbon containing feed stream, the hydrogen containing gas stream and the catalyst composition of this invention can be contacted in any suitable manner. Said two streams can be added separately into a suitable reaction vessel and then be contacted in at least partially mixed form with the catalyst composition under suitable reaction conditions. Or the two streams can be premixed and then contacted with the catalyst composition under suitable reaction conditions so as to produce a reaction product comprising at least one monoolefin (in the first embodiment) or cycloolefin (in the second embodiment).

The process of this invention can be conducted as a batch process or a continuous process. In a batch process, the process ingredients are added in any order to a vessel, preferably equipped with agitating and heating means, and the ingredients are then kept in contact for a certain length of time under suitable reaction conditions so as to produce a product comprising at least one monoolefin or cycloolefin. In this type of operation, the catalyst can be dispersed in the hydrocarbon containing feed (preferably liquid) and contacted with a free hydrogen containing gas with agitation (e.g., by means of a mechanical mixer or static mixing means); or the hydrocarbon containing feed (preferably liquid) and the free hydrogen containing gas can be circulated through a fixed bed containing the catalyst composition. In a continuous process, which is presently preferred, the hydrocarbon containing feed stream (preferably liquid) and the free hydrogen containing gas stream can be passed, at least partially mixed, through a fixed bed containing the solid catalyst composition, under such conditions as will result in a product comprising at least one cycloolefin. Optionally, an inert solvent can be present during the batch or continuous process.

Heating of the process ingredients can be required to accomplish at least partial conversion (preferably exceeding 50%) of the feed hydrocarbon to the olefin and cycloolefin, respectively. Any suitable temperature that will cause and maintain a controllable reaction can be employed. Any feasible heating means, if necessary, can be utilized. It is within the scope of this invention to preheat one or more of the process ingredients before they are introduced into a reactor. The reaction temperature generally exceeds about 40° F. and preferably ranges from about 60° F. to about 200° F.

The total reaction pressure can be atmospheric (about 15 psia) or higher. The selection of the reaction pressure will greatly depend on the reaction temperature, the feed rates of liquid feed and hydrogen gas and the specific reactor design. Generally, the total reaction pressure ranges from about 15 to about 5000 psia, preferably about 15 to about 1000 psia. Preferably, the reaction pressure is high enough so as to keep the hydrocarbon containing feed stream as a substantially liquid phase.

The reaction time, i.e., the time of intimate, simultaneous contact of all process ingredients, can vary from 1 minute to about 50 hours and will preferably be in the range of about 0.2 to about 2 hours. The actual reaction time will greatly depend on the flow rates of the hydrocarbon feed stream and of the free hydrogen containing gas stream, the selection of an effective, yet safe, reaction temperature, the extent of mixing and agitation (if any) during the reaction, and the amount of the catalyst employed.

Any suitable molar ratio of hydrogen to feed hydrocarbon can be employed. The amount of hydrogen charged to the reactor is chosen so as to initiate and maintain a suitable, safe rate of reaction under specific reaction conditions. The mol ratio of initially charged hydrogen to the feed hydrocarbon (alkadiene, alkatriene, cycloalkadiene or cycloalkatriene) can vary over a wide range such as about 0.05:1 to about 200:1, but will typically be in the range of about 5:1 to about 20:1 in a continuous flow system.

In a preferred embodiment, the amount of lithium methoxide employed ranges from about 10 mg to about 40 mg per mL of liquid hydrocarbon feed (preferably 1,5-cyclooctadiene) at room temperature and atmospheric pressure. The amount of CO gas, if added, is small in comparison with the amount of hydrogen charged. The mole ratio of CO to $H_2$ generally is less than about 1:100 (e.g., 1:500–1:150).

The formed reaction products, which comprise at least one monoolefin (first embodiment) or cycloolefin (second embodiment) can be separated from the reaction mixture by any suitable separation means such as fractional distillation, or crystallization, or extraction with a suitable solvent. Unreacted process ingredients can be recycled to the reaction zone with added fresh process ingredients.

The monoolefins (alkenes) prepared in accordance with the first embodiment of this invention are generally used as monomers for polymerization reactions. The cycloolefins prepared in accordance with the second embodiment of this invention can be converted to alkenes by ring opening, or they can be used as reactants in polymerization or epoxidation reactions, or they can be oxidized, e.g., to aliphatic dicarboxylic acids.

The following examples are presented to further illustrate this invention without unduly limiting the scope of the invention.

EXAMPLE I

This example illustrates the preparation of the supported palladium catalysts employed in the process of this invention.

Invention Catalyst A was prepared as follows. 375 grams of $Al(NO_3)_3.9H_2O$ and 50 cc of water were heated to about 60° C. so as to produce a first solution. 132 grams of $(NH_4)_2HPO_4$ and 50 cc of water were added to the first solution with heating and stirring so as to produce a second, clear solution. The second solution was added to a third solution made by mixing 250 cc of 29% $NH_4$ with 1 liter of water. A white aluminum phosphate gel was formed, which was aged by heating of the entire reaction mixture at 200° F. for 1 hour. The mixture was then filtered through a Buchner funnel. The filter cake was dried in a forced air oven at about 200° F. several hours and then calcined at about 700° F. for about 4 hours. The Al:P mole ratio of the aluminum phosphate was about 1:1; its pore volume was about 1.5 cc/g (measured by alcohol absorption as described below), and its surface area was about 100 $m^2/g$ (measured by $BET/N_2$, ASTM D3037). 7.0 grams of the calcined $AlPO_4$ were impregnated with a solution of 0.075 grams of palladium(II) acetate in enough acetone so as to completely wet $AlPO_4$. The thus impregnated catalyst material was dried at about 200° F. for about 1 hour and then reduced by hydrogen gas at about 500° F. for about 1 hour.

Control Catalyst B was prepared by impregnating 7.0 grams of Katalco alumina ($BET/N_2$ surface area: about 100 $m^2/g$; provided by Katalco Corporation, Chicago, Ill.) with a solution of 0.075 grams of Pd(II) acetate in acetone, drying and reducing as described above.

The above-cited alcohol absorption test was carried out in accordance with the following general test procedure: "A centrifuge tube having a porous bottom is filled with a sample of a weighed solid material and enough isopropanol to cover this solid material completely. The thus filled tube is rotated at room temperature and atmospheric pressure in a centrifuge for several minutes at a high speed, so as to remove all excess isopropanol (that is not absorbed by the solid material) through the porous bottom of the tube. Then the tube containing the solid material plus absorbed alcohol is weighed again. From the increase in weight (due to absorbed isopropanol) and the density of isopropanol, the pore volume of the solid material is calculated."

EXAMPLE II

This example illustrates the selective hydrogenation of 1,5-cyclooctadiene (1,5-COD) to cyclooctene in the presence of the supported palladium catalysts A and B.

0.5–1.0 gram of each catalyst was placed into a flask equipped with a stirring bar, a vacuum connection and a hydrogen source. The flask was repeatedly filled with $H_2$ and evacuated. Then 15–20 cc of a 20 weight-% solution of 1,5-cyclooctadiene (provided by Aldrich Chemical Company, Milwaukee, Wis.) in cyclohexane as solvent was added and thereafter hydrogen gas was introduced. This reaction mixture in the flask was stirred at room temperature and atmospheric pressure. Samples were taken at various intervals and analyzed by gas chromatography. Test results are summarized in Table I.

TABLE I

| Catalyst | Run 1 (Invention) Pd/AlPO$_4$ | | Run 2 (Control) Pd/Al$_2$O$_3$ | |
|---|---|---|---|---|
| Sample No. | % Conversion of 1,5-COD | % Selectivity to Cyclooctene | % Conversion of 1,5-COD | % Selectivity to Cyclooctene |
| 1 | 6.9 | 99.7 | 19.8 | — |
| 2 | 23.1 | 99.2 | 38.3 | — |
| 3 | 52.6 | 98.9 | 52.3 | — |
| 4 | 85.2 | 98.8 | 67.7 | 98.8 |
| 5 | 93.5 | 98.3 | 79.2 | 98.5 |
| 6 | 95.6 | 97.8 | 88.3 | 97.8 |
| 7 | 96.1 | 97.8 | 93.0 | 97.4 |
| 8 | 99.0 | 96.4 | 96.1 | 97.0 |
| 9 | 99.8 | 95.6 | 98.4 | 96.3 |
| 10[1] | 99.9+ | 93.0 | 99.9+ | 93.7 |
| 11[1] | — | — | ~100 | 86.8 |

[1] The conversion in samples 10 and 11 was estimated because it was difficult to determine it accurately.

Data in Table I are plotted in FIG. 1, which clearly shows that at equal conversions, the selectivity to the cycloolefin was higher for invention Catalyst A (Pd/AlPO$_4$; run 1) than for control Catalyst B (Pd/Al$_2$O$_3$; run 2).

EXAMPLE III

In this run (Run 3), a mixture of 15 cc of a 20 weight-% 1,5-cyclooctadiene solution in cyclohexane and about 50 mg of lithium methoxide was stirred with hydrogen gas for about 1.5 hours at room temperature and atmospheric pressure. Then 1.0 gram of Catalyst A (Pd/AlPO$_4$) and hydrogen gas were added to the above mixture, and the mixture was again stirred at room temperature and atmospheric pressure (about 70° F./14.7 psia). During this run, 1 cc of CO gas was charged to the reactor. This proved to be too much CO, so the system was partially evacuated and then refilled with hydrogen, and the run was continued. Test results of Run 3 are summarized in Table II.

TABLE II

| Sample No. | CO Present | % Conversion of 1,5-COD to 1,4-COD | % Conversion of 1,5-COD to Olefins | % Selectivity to Cyclooctene[1] |
|---|---|---|---|---|
| 1 | No | 15.5 | 56.6 | 99.6 |
| 2 | No | 12.9 | 74.8 | 99.5 |
| 3 | Yes | 13.3 | 76.6 | 99.4 |
| 4 | Yes | 9.1 | 86.6 | 99.3 |
| 5 | Yes | 3.3 | 94.5 | 98.8 |
| 6 | Yes | 1.4 | 97.9 | 98.2 |
| 7 | Yes | 0.5 | 99.3 | 97.9 |
| 8 | Yes | 0.1 | 99.9 | 97.2 |

[1] Cyclooctene yield divided by total yield of cyclooctene and cyclooctane.

A cursory comparison of the data of run 3 in Table II with those of invention run 1 (Table I) indicates that the selectivity to cyclooctene at comparable conversion of 1,5-cyclooctadiene to cycloolefins was higher in run 3, which employed lithium methoxide and lithium methoxide plus CO, respectively, in addition to the Pd/AlPO$_4$ catalyst.

In order to more quantitatively compare the results of Run 3 with those of Runs 1 and 2, the natural logarithm of $1/(1-f)$ was determined, wherein f is the conversion (expressed as a decimal fraction) of 1,5-COD. Values of $\ln(1/(1-f))$ and corresponding selectivities to cyclooctene were tabulated in Table III and were then plotted in FIG. 2.

TABLE III

| Run | Conversion f | $\ln \frac{1}{(1-f)}$ | % Selectivity to Cyclooctene |
|---|---|---|---|
| 1 | 0.231 | 0.26 | 99.2 |
| (Invention) | 0.526 | 0.75 | 98.9 |
| | 0.852 | 1.91 | 98.8 |
| | 0.935 | 2.73 | 98.3 |
| | 0.956 | 3.12 | 97.8 |
| | 0.961 | 3.24 | 97.8 |
| | 0.990 | 4.61 | 96.4 |
| | 0.998 | 6.21 | 95.6 |
| 2 | 0.677 | 1.13 | 98.8 |
| (Control) | 0.792 | 1.57 | 98.5 |
| | 0.883 | 2.15 | 97.8 |
| | 0.930 | 2.66 | 97.4 |
| | 0.961 | 3.24 | 97.0 |
| | 0.984 | 4.14 | 96.3 |
| | 0.999 | 6.91 | 93.7 |
| 3 | 0.566 | 0.83 | 99.6 |
| (Invention) | 0.748 | 1.38 | 99.5 |
| | 0.766 | 1.45 | 99.4 |
| | 0.866 | 2.01 | 99.3 |
| | 0.945 | 2.90 | 98.8 |
| | 0.979 | 3.86 | 98.2 |
| | 0.993 | 4.96 | 97.9 |
| | 0.999 | 6.91 | 97.2 |

Figure 2:
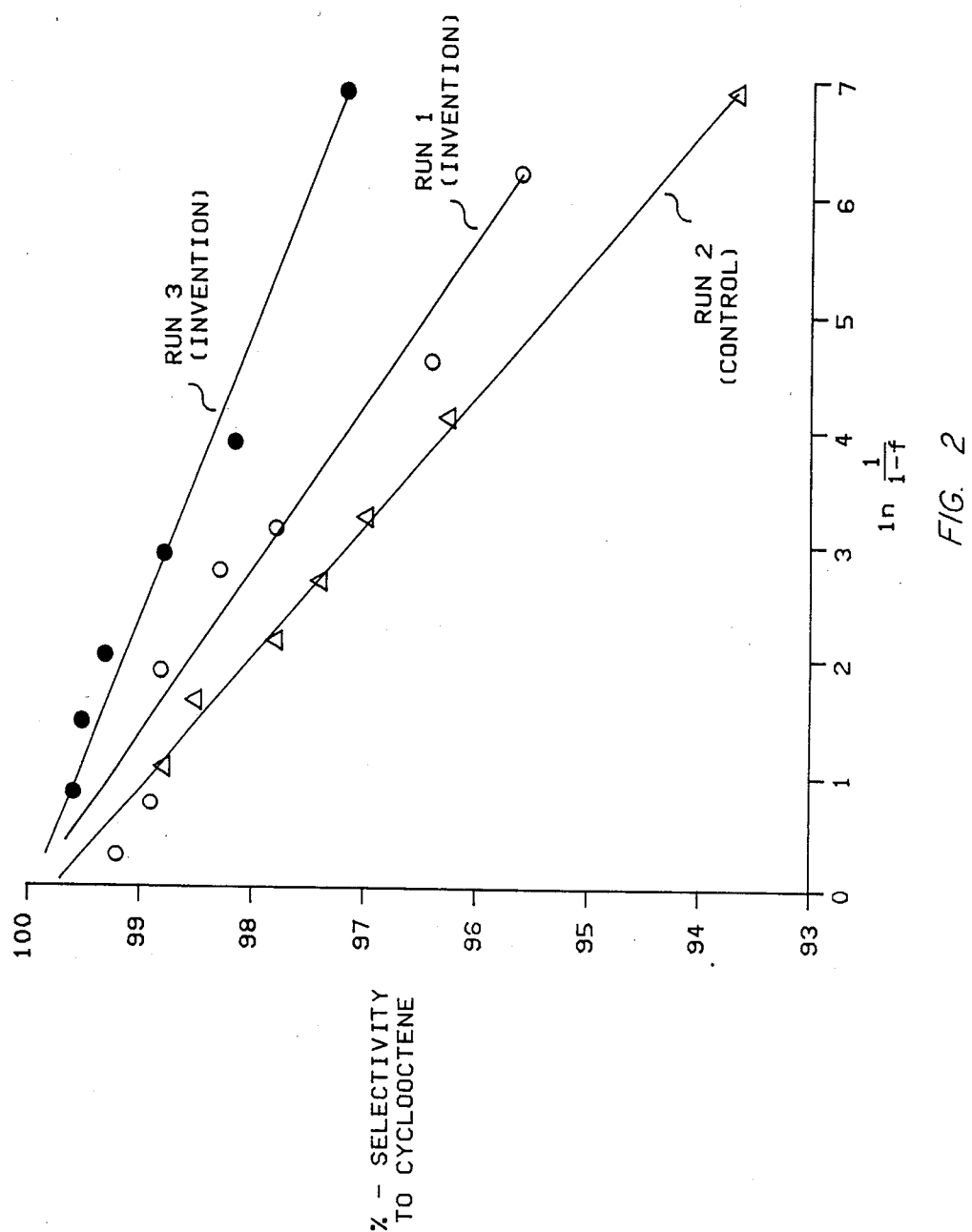
FIG. 2 is a graph showing the correlation of the natural logarithm of $1/(1-f)$ (wherein f is the conversion of cyclooctadiene) and the selectivity to cyclooctene.

The graphs plotted in FIG. 2 clearly show that the selectivity to cyclooctene was significantly higher, at comparable conversions of 1,5-cyclooctadiene, for Run 3 employing a Pd/AlPO$_4$ as solid catalyst plus lithium methoxide and carbon monoxide as additional catalytic ingredients, than for either invention Run 1 or control Run 2.

Reasonable variations and modifications are possible within the scope of the disclosure and appended claims.

We claim:

1. A process for preparing alkenes comprising the step of (A) contacting a feed stream comprising at least one hydrocarbon selected from the group consisting of alkadienes containing from 4 to 12 carbon atoms per molecule and alkatrienes containing from 6 to 12 carbon atoms per molecule with a free hydrogen containing gas, in the presence of a catalyst composition comprising (a) palladium metal and (b) an aluminum phosphate containing support, under such reaction conditions as will result in a reaction product comprising as major component at least one alkene having the same number of carbon atoms as said feed hydrocarbon, wherein the Al:P mol ratio of the aluminum phosphate ranges from about 0.4:1 to about 1.1:1.

2. A process in accordance with claim 1, wherein said catalyat composition has a palladium content ranging from about 0.01 to about 20 weight-%.

3. A process in accordance with claim 1, wherein said catalyst composition has a palladium content ranging from about 0.1 to about 10 weight-%, a surface area ranging from about 30 to about 200 m$^2$/g and a pore volume ranging from about 0.5 to about 3 cc/g.

4. A process in accordance with claim 1, wherein said reaction conditions comprise a reaction temperature in the range of from about 60° F. to about 200° F., a reaction pressure in the range of from about 15 psia to about 5,000 psia, and a reaction time in the range of from about 1 minute to about 50 hours.

5. A process in accordance with claim 1, wherein said contacting is carried out in the presence of carbon monoxide.

6. A process in accordance with claim 1, wherein said contacting is carried out in the presence of an alkali metal alkoxide containing from 1 to 4 carbon atoms per molecule.

7. A process in accordance with claim 5, wherein said contacting is carried out in the presence of an alkali metal alkoxide containing from 1 to 4 carbon atoms per molecule.

8. A process in accordance with claim 1 further comprising the step (B) of separating said alkene from said reaction product.

9. A process for preparing cycloalkenes comprising the step of (A) contacting a feed stream comprising at least one hydrocarbon selected from the group consisting of cycloalkadienes containing 5 to 12 carbon atoms per molecule and cycloalkatrienes containing 7 to 12 carbon atoms per molecule with a free hydrogen containing gas, in the presence of a catalyst composition comprising (a) palladium metal and (b) an aluminum phosphate containing support, under such reaction conditions as will result in a reaction product comprising as the major component at least one cycloalkene having the same number of carbon atoms as said feed hydrocarbon, wherein the Al:P mol ratio of the aluminum phosphate ranges from about 0.4:1 to about 1.1:1.

10. A process in accordance with claim 9, wherein said catalyst composition has a palladium content ranging from about 0.01 to about 20 weight-%.

11. A process in accordance with claim 9, wherein said catalyst composition has a palladium content ranging from about 0.1 to about 10 weight-%, the surface area of said catalyst composition ranges from about 30 to about 200 m$^2$/g, and the pore volume of said catalyst composition ranges from about 0.5 to about 3 cc/g.

12. A process in accordance with claim 9, wherein said catalyst composition has a palladium content ranging from about 0.2 to about 5 weight-%, the surface area of said catalyst composition ranges from about 50 to about 150 m$^2$/g and the pore volume of said catalyst composition ranges from about 1 to about 2 cc/g.

13. A process in accordance with claim 9, wherein said cycloalkadiene is 1,5-cyclooctadiene, and said cycloalkene is cyclooctene.

14. A process in accordance with claim 13, wherein said catalyst composition has a palladium content ranging from about 0.2 to about 5 weight-%, the surface area of said catalyst composition ranges from about 50 to about 150 m$^2$/g and the pore volume of said catalyst composition ranges from about 1 to about 2 cc/g.

15. A process in accordance with claim 14 wherein the Al:P mol ratio of said aluminum phosphate ranges from about 0.9:1 to about 1.1:1.

16. A process in accordance with claim 9, wherein said reaction conditions comprise a reaction temperature ranging from about 60° F. to about 200° F., a reaction pressure ranging from about 15 psia to about 5000 psia, and a reaction time ranging from about 1 minute to about 50 hours.

17. A process in accordance with claim 13, wherein said reaction conditions comprise a reaction temperature ranging from about 60° C. to about 200° C., a hydrogen reaction pressure ranging from about 15 psia to about 5000 psia, and a reaction time ranging from about 1 minute to about 50 hours.

18. A process in accordance with claim 17, wherein the reaction time ranges from about 0.2 to about 2 hours.

19. A process in accordance with claim 9, wherein said contacting is carried out in the presence of an alkali metal alkoxide containing 1 to 4 carbon atoms per molecule.

20. A process in accordance with claim 9, wherein said contacting is carried out in the presence of carbon monoxide.

21. A process in accordance with claim 19, wherein said contacting is carried out in the presence of carbon monoxide.

22. A process in accordance with claim 13, wherein said 1,5-cyclooctadiene containing feed stream contains lithium methoxide and said free hydrogen containing gas stream contains carbon monoxide.

23. A process in accordance with claim 9, comprising the additional step (B) of separating said at least one cycloalkene from said reaction product.

24. A process in accordance with claim 9, wherein said aluminum phosphate has been prepared by precipitation from a mixture of an aqueous solution of Al(NO$_3$)$_3$ and an aqueous solution of (NH$_4$)$_2$HPO$_4$ and said aluminum phospate has been impregnated with a solution of palladium(II) acetate in acetone, dried and heated with a reducing gas.

25. A process in accordance with claim 24, wherein said drying has been carried out at a temperature of about 100°–300° F. for about 0.1–10 hours, said heating with said reducing gas has been carried out at about 400°–300° F. for about 0.1–5 hours, and said reducing gas is a free hydrogen containing gas.

26. A process in accordance with claim 22, wherein the amount of lithium methoxide is in the range of from about 10 mg to about 40 mg per mL of liquid 1,5-cyclooctadiene, and the mol ratio of carbon monoxide to hydrogen is in the range of from about 1:500 to about 1:150.

* * * * *